Figure 1:
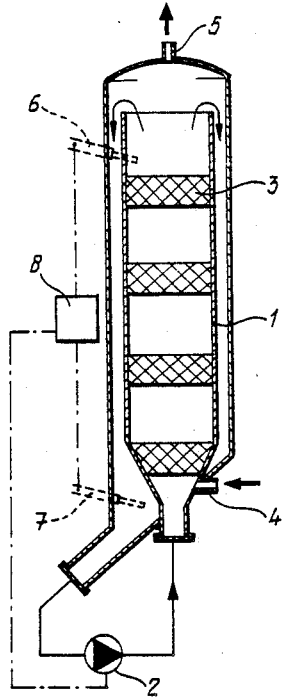

United States Patent [19]

Oosterhuis et al.

[11] Patent Number: 4,891,318

[45] Date of Patent: Jan. 2, 1990

[54] METHOD FOR THE FERMENTATIVE PREPARATION OF POLYSACCHARIDES, IN PARTICULAR XANTHANE

[75] Inventors: Nicolaas M. G. Oosterhuis, Roosendaal; Kees Koerts, Driebergen, both of Netherlands

[73] Assignee: Cooperatieve Vereniging Suiker Unie U.S., Netherlands

[21] Appl. No.: 59,590

[22] Filed: Jun. 8, 1987

[30] Foreign Application Priority Data

Jun. 9, 1986 [NL] Netherlands .......................... 8601495

[51] Int. Cl.⁴ ....................... C12P 19/04; C12P 19/06; C12R 1/64
[52] U.S. Cl. ................................... 435/104; 435/101; 435/315; 435/818; 435/901
[58] Field of Search ................. 435/104, 101, 810, 910

[56] References Cited

U.S. PATENT DOCUMENTS

| | | | |
|---|---|---|---|
| 3,616,260 | 10/1971 | Muller | 435/812 |
| 3,915,807 | 10/1975 | Boiko et al. | 435/812 |
| 3,957,585 | 5/1976 | Malick | 435/812 |
| 3,986,934 | 10/1976 | Muller | 435/812 |
| 4,019,962 | 4/1977 | Allen et al. | 435/247 |
| 4,207,180 | 6/1980 | Chang | 435/262 |
| 4,251,633 | 2/1981 | Orlowski et al. | 435/104 |
| 4,665,833 | 5/1987 | Buchwalder | 435/243 |

*Primary Examiner*—Herbert J. Lilling
*Attorney, Agent, or Firm*—Webb, Burden, Ziesenheim & Webb

[57] ABSTRACT

For the fermentative preparation of polysaccharides, in particular xanthane, water, production medium (sugars, nutrient salts), and an inoculation material of a suitable aerobic bacterium are mixed in a reactor as reaction components, the production medium being exposed to fermentation while an oxygen-containing gas is being supplied. The object is to avoid the usual low yield of such a process and to reject an expensive and sensitive alternative construction (circulation tube). According to the invention, the reaction components are introduced into a reactor vessel in a circulating flow by means of pumping means, which circulating flow comprises a rising flow and a descending flow which are separated from each other by one or more partitions disposed in the reactor vessel. The mixing is brought about because the rising flow and/or the descending flow is passed essentially in the form of a plug flow through one or more static in-line mixers.

5 Claims, 2 Drawing Sheets

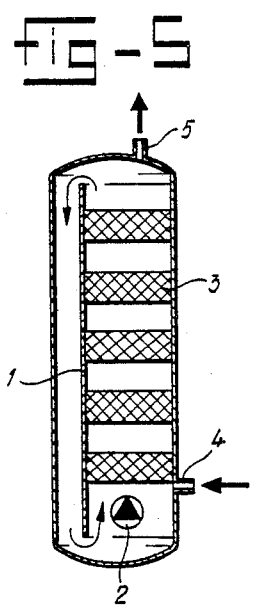
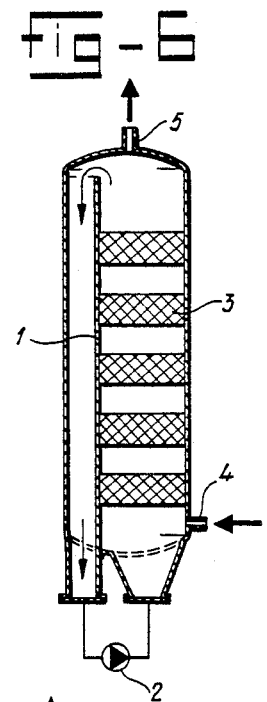
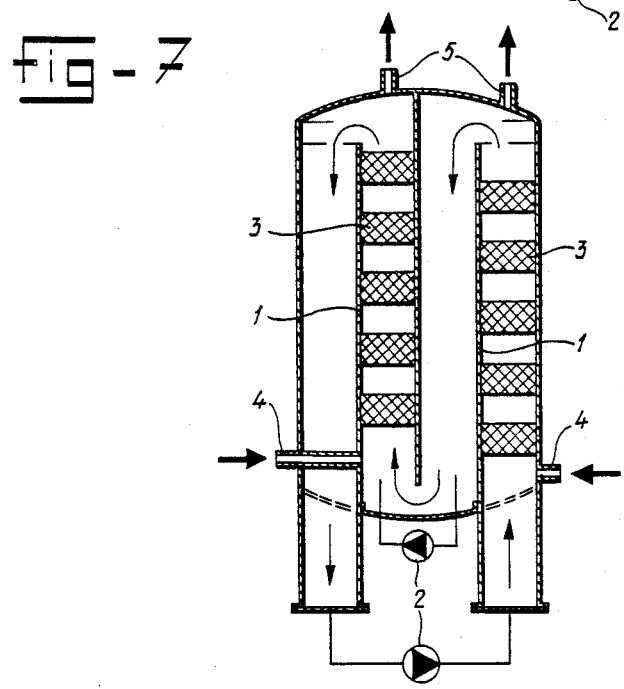

METHOD FOR THE FERMENTATIVE PREPARATION OF POLYSACCHARIDES, IN PARTICULAR XANTHANE

The invention relates in the first instance to a method for the fermentative preparation of polysaccharides, in particular xanthane, water, a production medium containing one or more sugars and nutrient salts, and an inoculation material of a suitable aerobic bacterium being mixed in a reactor vessel as reaction components and said medium being exposed to fermentation while oxygen-containing gas is being supplied.

It is usual to prepare polysaccharides in a so-called stirred vessel. It has been found that when such a vessel is used a considerable variation occurs in the circulation time, i.e. the time which a small element of liquid requires in order to be fed from the stirrer round the vessel and back to the stirrer. This variation has an unfavourable effect on the yield of the process since the liquid particles with a relatively rapid circulation time will be subjected for too short a time to the treatment (incomplete conversion), while liquid particles with a slow circulation time will be exposed to the treatment for too long a period. The viscosity increases during the fermentation process and from a certain value of viscosity upwards, the stirrer creates a revolving cylinder while the remainder virtually stands still. In addition, if a stirred vessel is used, a relatively high oxygen concentration will occur at the stirrer and a relatively low oxygen concentration at the vessel wall. These disadvantageous phenomena are intensified as the rheological properties of the mixture change: the mixture becomes more viscous. In order, nevertheless, to achieve as complete a conversion as possible, high energy costs are often necessary, the energy being used primarily for stirring. Another problem in carrying out a process in a stirred vessel is that increasing (scaling up) the equipment from the laboratory scale to the technical scale is accompanied by a large change in the conditions under which the process proceeds.

These drawbacks can be eliminated by using the method and equipment according to the not-prepublished European Patent Application 85 201 863.9. In that case, use is made of an endless circulation tube in which a circulating plug current is brought about, which current is passed through a number of in-line mixers. Because of the weakness of the construction, such a circulation tube is relatively expensive and sensitive, while the wall surface is relatively large in relation to the contents. The investment is therefore high.

According to the invention, it has now been found that the abovementioned drawbacks of a stirred vessel can be eliminated without using a relatively expensive, sensitive circulation tube and in particular, because the reaction components are introduced into the reactor vessel in a circulating flow by means of pumping means, which circulating flow comprises a rising current and a descending current, which flows are separated from each other by one or more partitions disposed in the reactor vessel, the mixing being brought about by passing the rising flow and/or the descending flow essentially in the form of a plug flow through one or more static in-line mixers.

Very reasonable results, which far exceed the results of a stirred vessel, can be achieved by using a constant circulation rate. In general, however, it is advisable to measure the concentration of a reaction component or a value derived therefrom at at least one point and to regulate the reaction rate within critical minimum and maximum limits on the basis of said measurement in accordance with the kinetics of the process.

The reaction rate of an enzymatic of microbiological process is understood to mean the rate at which a certain degree of chemical conversion is achieved. This may be the rate of a certain oxygen absorption, carboxylic acid production, heat generation, substrate consumption, product formation and the like. In general, it holds true that the reaction rate increases to a certain concentration of a reaction component ($C_{minimum,\ critical}$), then remains more or less constant up to a certain higher concentration of said component ($C_{maximum,\ critical}$), and finally decreases at concentrations of said component which are still higher. It will be clear that it is beneficial for the concentration of a component to be kept between the critical maximum and minimum concentration values while a process is being carried out. By using a vessel in which a plug current is maintained, inter alia, by means of in-line mixers, the concentration of the component or of several components can be kept between the critical values by controlling the reaction rate by means of one or more concentration measurements or measurements of values derived therefrom. In particular, the flow rate of the plug flow is suitable for being controlled on the basis of the measurement or measurements of the concentration of a component or a value derived therefrom. This flow rate determines, in fact, the contact time between the various reaction components, while transport parameters (gas-liquid; liquid-liquid; solid-liquid) are determined by the flow rate.

Attention is drawn to the fact that a method for carrying out a chemical reaction, in particular a biochemical reaction, is known from the published European Patent Application 0,111,253, which method is carried out in a reactor vessel which is divided into two chambers by a wall; no plug flow is brought about in the vessel. In-line mixers are not mentioned either. Nevertheless, the concentration of a reaction component, namely the reactioninhibiting component, is measured directly or indirectly and the supply of one or more new components to the reactor is regulated on the basis of said measurement so that a maximum is not exceeded.

In addition to choosing the regulation of the flow rate of the plug flow, it is possible to choose the regulation of the supply rate of a substrate, this being a reaction component which is used as a nutrient. An important substrate in the preparation of xanthane is oxygen. The result is that the concentration of the substrate directly downstream of the static mixers will be less than the critical maximum value, while immediately upstream of the static mixers, i.e. at the end of the circulation path, said value has to be higher than the critical minimum value. The reaction rate can be controlled by supplying, at a carefully chosen circulation rate of the plug flow, more or less substrate on the basis of measurements of the substrate concentration. To achieve energy saving, it is, however, preferable to control the reaction rate with a carefully chosen substrate supply by regulating the flow rate of the plug flow on the basis of the measurements of the concentration of a reaction component or a value derived therefrom. Incidently, the possibility is not ruled out of controlling the reaction rate by simultaneouslys regulating the plug flow rate and the supply of a reaction component.

Inter alia, the number of substrate injection points and the dimensioning of the static mixing elements and the number thereof also have an effect on the process. For a particular equipment, however, these are usually fixed and therefore are usually unsuitable for subjection to regulation.

Essential for the effect of the invention is that both the optimization of the reactor and the control of the process conditions are determined by the reaction kinetics.

Use of static mixers has the advantage that relatively little energy is consumed and that the reaction volume can be relatively small, while the liquid moves as a plug flow.

Instead of the concentration of a reaction component itself, a value derived therefrom may be measured, the pH, the oxygen tension, the temperature and the like being suitable, depending on the process.

The invention also relates to a reactor vessel for the fermentative preparation of polysaccharides, in particular xanthane. In order to be able to carry out the method according to the invention, the vessel is divided by one or more essentially vertical partitions into descending and rising sections, static in-line mixers are disposed in at least one of said sections and pumping means are present inside or outside of the vessel in order to bring about a circulating flow with rising and descending flow in the vessel.

The partition may be cylindrical, the vessel being divided into a cylindrical section and an annular section.

Another possibility is that the partition or the partitions are straight or slightly bent.

In order to be able to regulate the process between critical minimum and maximum reaction rates, the reactor vessel will have at least one measuring element for measuring the concentration of one or more reaction components or a value derived therefrom, while regulating means are present for regulating the pump speed depending on the measured value. Preferably, the reactor vessel is provided at at least one point with measuring elements for measuring the essentially maximum and the essentially minimum concentration of a reaction component or a value derived therefrom.

The fermentation liquid acquires structural properties, in particular pseudoplasticity, in the process of preparing polysaccharides by means of aerobic bacteria. At any rate, a pump is necessary for the circulation in the case of mixtures which become viscous. In the preparation of microbial polysaccharides in which the viscosity remains below a certain value, the circulation may also be brought about by injecting a substrate, in particular the gas mixture used.

The most important advantage of the invention is that, while retaining a relatively cheap, strong reactor vessel, the product yield is appreciably higher for the same energy consumption than in a stirred vessel. If a stirred vessel is used, it is necessary to stop at a point at which the product yield is still relatively low in view of the considerable rise in viscosity. This limitation exists to a much lesser degree in the method according to the invention.

Embodiments of reactor vessels to be used in the method according to the invention will now be explained in more detail by reference to the figures.

The reactor vessels of usual cylindrical shape shown in the figures are intended for the preparation of polysaccharides, xanthane being considered in particular. Reaction components are water, a production medium which contains one or more sugars and nutrient salts and an inoculation material of a suitable aerobic bacterium, in the case of xanthane preparations: Xanthamonas compestris. These components are mixed in a reactor vessel for a certain time, for example 72 hours, at a certain temperature, for example 30° C. and a certain pH, for example 7, while air is being supplied, a polysaccharide being formed by fermentation.

The reactor vessels are not the usual stirred vessels, but in each of the vessels there are disposed one or more vertical partitions 1 which separate the vessel chamber into a number of subchambers in which a circulation is brought about by means of a pump 2. The said subchambers form the boundaries of rising and descending flows.

The arrows in the figures indicate in which subchamber a rising flow or a descending flow is generated. At least one of the subchambers in each vessel contains a number of static in-line mixers 3, for example of a construction described in the Dutch Patent Application 75.02953, 77.00090 or 80.04240. Said mixers 3 divide the main flow into subflows, interchange the mutual position of the subflows and then combine the subflows. If necessary, a heating or cooling unit may be added to each vessel to keep the temperature at a desired value (for example, 30° C.). Incidentally, heat is liberated during the fermentation process. Such a heating or cooling unit may, for example, consist of a double vessel jacket with an inlet and a discharge for heating or cooling medium.

The air inlet of each vessel is indicated by 4 and the discharge for the gas mixture formed in the fermentation process by 5.

In FIG. 1, the partition 1 is cylindrical. The rising flow of the circulation flow is situated inside the partition 1, while the descending flow is present in the annular chamber between the vessel wall and the partition 1. The pump 2 is sited outside the vessel. The static mixers 3 are sited in the rising flow. They have a double function: they mix the constituents of the liquid in a direction transverse to the flow direction and they disperse the gas phase in a manner such that an increased mass transfer occurs in the mixers. The pump speed is chosen so that a certain circulation time is achieved with adequate mass transfer taking place.

To promote the uniformity of the descending flow, the annular chamber between the partition 1 and the vessel wall might be provided, for example, with a spiral guide.

Figure 2:
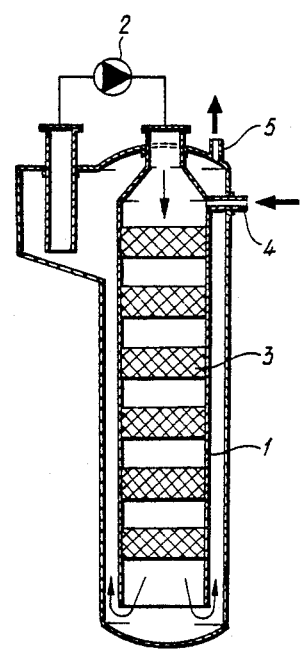

FIG. 2 differs from FIG. 1 in that the descending flow is passed through the cylindrical internal chamber, which is provided with static mixers, of the partition 1, while the rising flow is passed through the annular chamber.

Figure 3:
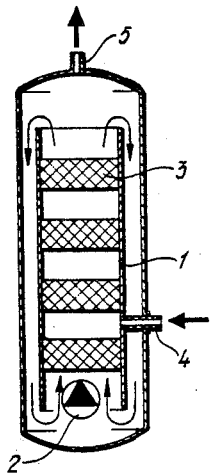
Figure 4:
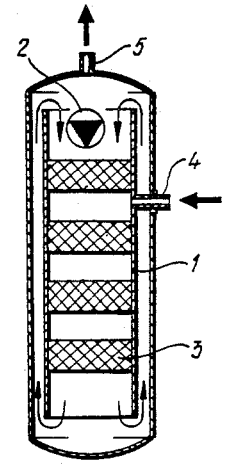

FIG. 3 differs from FIG. 1 and FIG. 4 differs from FIG. 2 in that the circulation pump 2 is sited in the vessel.

One of the problems in choosing a suitable pump may be that the polysaccharide formed, for example xanthane, is pseudoplastic. A centrifugal pump with a vermiform impeller or a pump with combined axial and centrifugal action are suitable for solving this problem.

FIG. 5 shows a reactor vessel which is divided into two sections of unequal size by a straight partition. The largest section is provided with static in-line mixers 3 and forms the boundary of the rising flow during operation.

FIG. 6 differs from FIG. 5 in that the pump is outside the reactor vessel.

FIG. 7 shows an embodiment with three straight partitions which, together with the vessel wall 4, form the boundary of subchambers, of which two are used for a rising flow and two for a descending flow. The subchambers intended for the rising flow are provided with static in-line mixers 3. Two pumps 2 may be necessary. The advantage of this embodiment is that the height:diameter ratio can be relatively low.

In general the reactors operate in a batchwise manner, although some types, in particular the types in which the subchamber(s) with static mixers is (are) used for a rising flow, are also suitable for continuous supply and discharge of reaction components.

In order to cause a reactor to function according to the invention, it is completely field with said reaction components and the pump is switched on, air being supplied via the inlet 4 as substrate. An intimate mixing of the reaction components takes place in the static mixers. The components are partially consumed by the aerobic bacteria, as a result of which the bacteria multiply and excrete a product. Use is made of the atmospheric oxygen as substrate and said oxygen is consumed by the aerobic bacteria. After mixing, excess gas will have to be separated off, for example by a liquid-gas separator. The gas separated off is discharged at 5.

A plug flow is brought about at least in the section in which the static mixers are situated. The possibility is not excluded that supply elements are sited between the static mixers in order to be able to supply certain components.

Of essential importance is the fact that the conditions under which the reaction takes place can be optimized regardless of the size of the reactor and that the energy consumption can be limited to a minimum. The scaling up of the process is facilitated because the course of the process in the reactor can be described well and consequently modelled. Microbial polysaccharides have the property that they have a considerable effect on the rheology of the medium. An energy saving is always achieved with respect to a stirred vessel.

Good results can also be achieved with a constant circulation rate in the preparation of polysaccharides. It is preferable, however, to measure the concentration of a reaction component or a value derived therefrom at one or more points and to regulate the reaction rate on the basis of said measurement. By way of example, FIG. 1 shows how the regulating circuit could be embodied. At the top end of the rising section 1 there is situated a measuring electrode 6, while a measuring electrode 7 is disposed at the bottom end of the descending section 2. Said measuring electrodes are connected to a regulating unit 8 which controls the pump 2 in a manner such that the reaction rate settles down within critical minimum and maximum limits. In particular, the measuring electrode 6 will be used to determine the maximum substrate concentration after mixing, while the purpose of the measuring electrode 7 is to determine the minimum substrate concentration. To achieve an optimum reaction rate, the plug flow rate will be adjusted by the pump so that the concentration of the substrate always settles down within a maximum and minimum critical value. Specifically, all this means that, if the measuring electrode 6 determines that the maximum substrate concentration settles down above the critical maximum value, the pump speed will be reduced, while if the measurement made by the measuring electrode 7 shows that the minimum substrate concentration settles down below the critical minimum, the pump speed will be increased.

The measuring electrodes measure the concentration of the substrate or of another reaction component itself or a value which is a direct function of said concentration. For which purpose, inter alia, the pH, the oxygen tension, the temperature and the pressure are suitable, regardless of the process.

The pump speed is regulated in order to cause the reaction to have an optimum course. The possibility is not ruled out, however, that the pump speed is constant and that the supply rate of substrate and/or other reaction components is regulated on the basis of the measurements of the concentration or values derived therefrom. Injection can take place at more points and the number of injection points may be varied on the basis of said measurements. Regulation of the product discharge rate is also among the possibilities.

Essential for the invention is the fact that the process can take place in a normal, robust and relatively cheap reactor vessel which is divided by at least one partition into subchambers. Moreover, it is essential that a circulation flow is brought about in the subchambers with a rising flow and a descending flow and that at least one of said flows is passed in the form of a plug flow through one or more static in-line mixers.

EXAMPLE

Xanthomonas campestris ATCC 13951 is cultivated for 48 h at 30° C. on a tryptone glucose yeast extract agar. Material from a separately situated colony is inoculated into a flask containing glucose yeast extract malt extract solution and suspended, and cultivation is carried out for 24 h at 30° C. while shaking. 1 l of this inoculation material is added to 25 l of fermentation medium containing glucose as a source of carbon in a concentration of 4% by weight and yeast extract as an organic source of nitrogen in a concentration of 0.5% by weight. Magnesium ions are added as $MgSo_4$ in a concentration of 0.05% by weight. The pH is kept constant during the fermentation between 6.5 and 7.5 by adding KOH in a concentration of 2 N. A basic buffer is used in the form of $K_2HPO_4$ in a concentration of 0.2% by weight. This material was situated in a reactor vessel as described above having a volume of 120 l. The circulation time was 8 min so that the circulation rate was 15 l/min. The temperature was 31° C. and 40 l of air were supplied per minute. The circulation of the material was continued for 72 h. It was found that 5 to 6% by weight of xanthane was formed, 4 kW of energy being consumed per $m^3$ of reactor volume. With the same energy input (4 $kW/m^3$) the fermentation takes 144 hours in a stirred vessel (on a 120 l scale). The product concentration achieved in that case is 3% by weight. On a pilot plant scale this product concentration is achieved using a stirred vessel with an energy input of 4–5 $kW/m^3$ in 144 h. A much lower product concentration, namely 1.8 to 2.0% is achieved, however, with said energy input in 72 h.

We claim:

1. Method for the fermentative preparation of polysaccharides, water, a production medium containing one or more sugars and nutrient salts, and an inoculation material of a suitable aerobic bacterium being mixed in a reactor vessel as reaction components and said medium being exposed to fermentation while air is being supplied, characterized in that the reaction components are introduced into the reactor vessel in a circulating flow by means of pumping means, which circulating flow comprises a rising flow and a descending flow, which flows are separated from each other by one or more partitions disposed in the reactor vessel, the mixing being brought about by passing the rising flow and/or the descending flow essentially in the form of a plug flow through one or more static in-line mixers.

2. Method according to claim 1, characterized in that the concentration of a reaction component or a value derived therefrom is measured at at least one point and the reaction rate is regulated within critical minimum and maximum limits on the basis of said measurement in accordance with the kinetics of the process.

3. Method according to claim 2, characterized in that the reaction rate is regulated by means of regulating the flow rate of the plug flow in the circulation tube.

4. Method according to claim 2, characterized in that the reaction rate is regulated by means of regulating the supply of reaction components to the circulation tube.

5. Method according to claim 1, wherein said polysaccharide is xanthane.

* * * * *